US009488551B2

(12) United States Patent
Iraneta et al.

(10) Patent No.: US 9,488,551 B2
(45) Date of Patent: Nov. 8, 2016

(54) DRIED SAMPLE CARRIER HAVING DISSOLVABLE SAMPLE REGIONS

(71) Applicant: WATERS TECHNOLOGIES CORPORATION, Milford, MA (US)

(72) Inventors: Pamela C. Iraneta, Brighton, MA (US); Kevin D. Wyndham, Upton, MA (US); Moon Chul Jung, Arlington, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 112 days.

(21) Appl. No.: 14/375,337

(22) PCT Filed: Feb. 1, 2013

(86) PCT No.: PCT/US2013/024328
§ 371 (c)(1),
(2) Date: Jul. 29, 2014

(87) PCT Pub. No.: WO2013/122754
PCT Pub. Date: Aug. 22, 2013

(65) Prior Publication Data
US 2014/0373644 A1 Dec. 25, 2014

Related U.S. Application Data

(60) Provisional application No. 61/598,502, filed on Feb. 14, 2012.

(51) Int. Cl.
*G01N 1/00* (2006.01)
*G01N 1/40* (2006.01)
(Continued)

(52) U.S. Cl.
CPC ............... *G01N 1/00* (2013.01); *B01L 3/5025* (2013.01); *B01L 3/5635* (2013.01); *G01N 1/10* (2013.01);
(Continued)

(58) Field of Classification Search
CPC ........................................................ G01N 1/00
USPC .......... 73/863.23, 864.91; 422/551; 435/40.5
See application file for complete search history.

(56) References Cited

U.S. PATENT DOCUMENTS

| 5,432,097 | A | 7/1995 | Yourno |
| 5,638,170 | A | 6/1997 | Trinka et al. |
| 2005/0276728 | A1 | 12/2005 | Muller-Cohn et al. |
| 2011/0008771 | A1 | 1/2011 | Hanselle et al. |
| 2013/0116597 | A1 | 5/2013 | Rudge et al. |

FOREIGN PATENT DOCUMENTS

| DE | 10103196 A1 | 7/2002 |
| WO | 2010043668 A1 | 4/2010 |

(Continued)

OTHER PUBLICATIONS

Extended Search Report in counterpart European Patent Application No. 13749488.6, mailed on Sep. 28, 2015; 10 pages.
(Continued)

*Primary Examiner* — Laura Martin
*Assistant Examiner* — Jean Morello
(74) *Attorney, Agent, or Firm* — Schmeiser, Olsen & Watts LLP; William G. Guerin

(57) ABSTRACT

Described are sample carriers and methods of extracting a fluid sample from a dried sample on a sample carrier. The sample carrier has a first carrier portion that receives a fluid sample, and includes a material that adsorbs the fluid sample and dissolves upon application of a solvent. A second carrier portion is attached to the first carrier portion and includes a material that is indissolvable in the solvent. The first carrier portion having a dried sample is dissolved into a solution upon application of the solvent. The solution can be analyzed to determine constituents in the extracted sample. The sample carrier can conveniently be in the form of a card or a dipstick. In alternative embodiments, a carrier portion that includes the dried sample is indissolvable in the solvent but is released from another carrier portion through application of a solvent to an intervening dissolvable carrier portion.

36 Claims, 9 Drawing Sheets

(51) Int. Cl.
*G01N 33/49* (2006.01)
*G01N 1/10* (2006.01)
*B01L 3/00* (2006.01)
*G01N 1/28* (2006.01)
*G01N 35/00* (2006.01)

(52) U.S. Cl.
CPC .............. *G01N 1/28* (2013.01); *G01N 1/4055* (2013.01); *G01N 33/49* (2013.01); *B01L 2300/069* (2013.01); *B01L 2300/087* (2013.01); *B01L 2300/0851* (2013.01); *B01L 2300/12* (2013.01); *B01L 2400/0677* (2013.01); *G01N 2001/288* (2013.01); *G01N 2001/4061* (2013.01); *G01N 2035/00108* (2013.01)

(56) References Cited

FOREIGN PATENT DOCUMENTS

| WO | 2011153122 A2 | 12/2011 |
| WO | 2013067520 A1 | 5/2013 |
| WO | 2014008060 A1 | 1/2014 |

OTHER PUBLICATIONS

International Preliminary report on Patentability in related international patent application No. PCT/US13/24328, mailed on Aug. 28, 2014; 7 pages.

International Search Report & Written Opinion in counterpart international patent application No. PCT/US13/24328, mailed on Apr. 15, 2013.

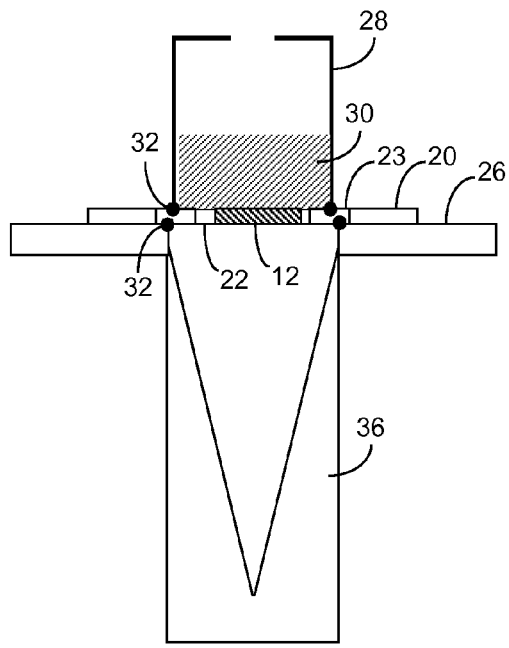 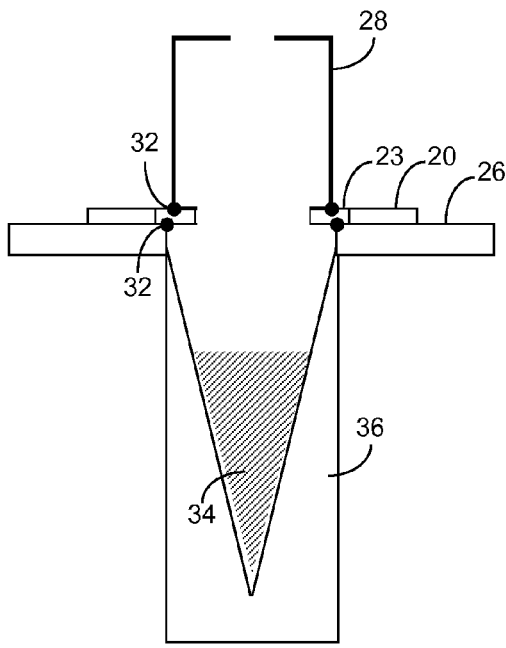
*FIG. 3A*    *FIG. 3B*
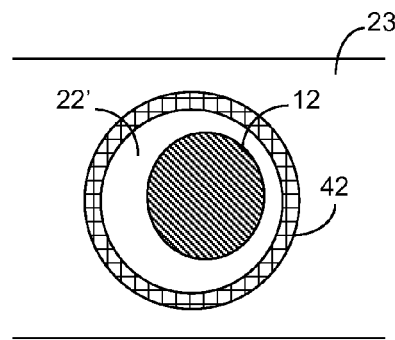 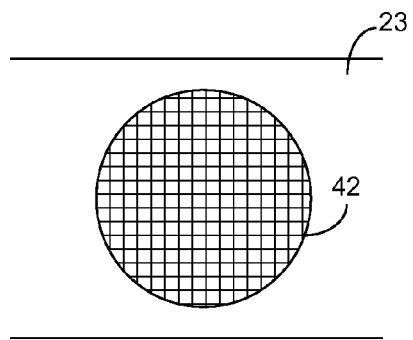
*FIG. 5A*    *FIG. 5C*
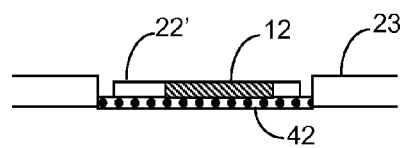 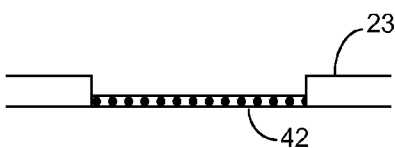
*FIG. 5B*    *FIG. 5D*

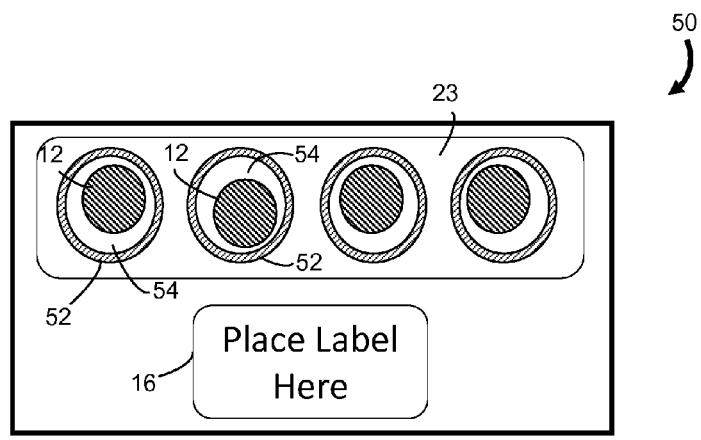
FIG. 6
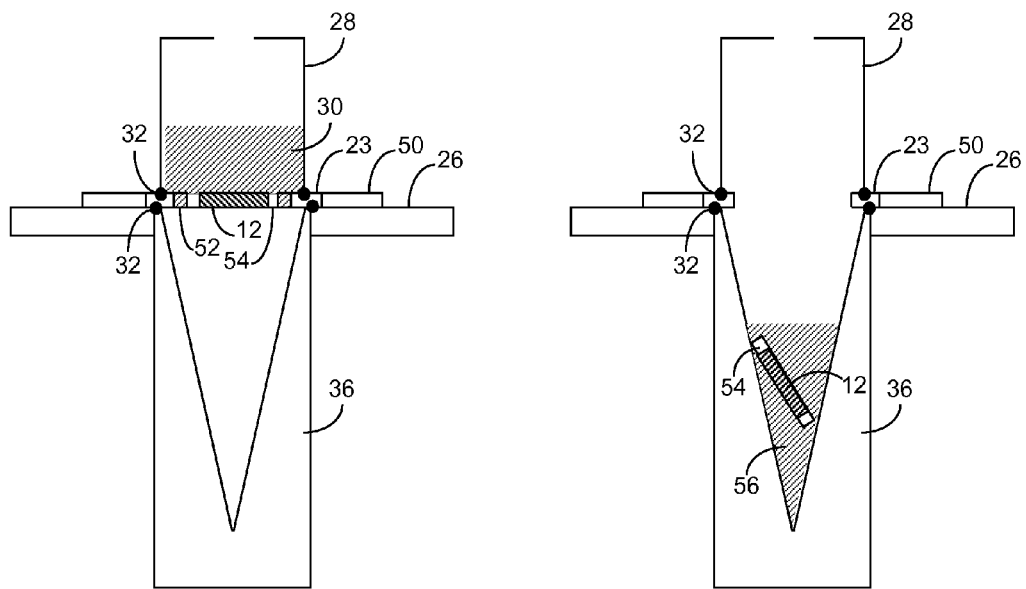
FIG. 7A  FIG. 7B

DRIED SAMPLE CARRIER HAVING DISSOLVABLE SAMPLE REGIONS

RELATED APPLICATION

This application claims the benefit of the earlier filing date of U.S. Provisional Patent Application Ser. No. 61/598,502, filed Feb. 14, 2012 and titled "Dried Sample Carrier Having Dissolvable Sample Collection Regions," the entirety of which is incorporated herein by reference.

FIELD OF THE INVENTION

The invention relates generally to analyses of dried biological fluids such as dried blood spots. More particularly, the invention relates to collection media for biological fluids and the extraction of previously dried samples from the collection media.

BACKGROUND

Measuring concentrations of administered drugs and their metabolites in biological fluids, such as whole blood, plasma and serum, is important to understanding the efficacy and toxicological effects of the drugs. Typical clinical studies require handling and processing large numbers of biological fluid samples at low temperature with special care. Dried spot sampling is an alternative to the current practice and is based on collection of small volumes (e.g., several microliters or less) of biological fluids as dried spots. For example, dried blood spot (DBS) sampling involves the collection of small volumes of blood on a carrier medium. The reduced sample size and the convenience of compact carrier mediums results in easier sample handling and reduced shipping costs. Samples are reconstituted from the dried spots using suitable solvents during an extraction process. The reconstituted samples can be analyzed, for example, in a liquid chromatography-mass spectrometry (LC-MS) assay.

In many instances, the above technique fails to deliver a desirable detection sensitivity and ease of use. The dried spots can vary in analyte concentration due, for example, to the hematocrit of the subject. To improve repeatability, sampling of the entire dried spot is generally required. Conventional techniques include punching the dried spots from sample cards. Typical punching processes use a sharp punch tool. Repeated use of the punch tool can lead to carryover. Moreover, the process of punching the spots is tedious for the clinician and can be a limiting step in the overall work flow.

SUMMARY

In one aspect, the invention features a sample carrier for storing a dried sample of a received fluid. The sample carrier includes a first carrier portion and a second carrier portion. The first carrier portion is configured to receive a fluid sample and includes a material that adsorbs the fluid sample and dissolves upon application of a solvent. The second carrier portion is affixed to the first carrier portion and includes a material that is indissolvable in the solvent. The first carrier portion and a dried sample contained therein are dissolved into a solution upon application of the solvent to the first carrier portion.

In another aspect, the invention features a method of extracting a fluid sample from a dried sample. A first carrier portion of a sample carrier is dissolved into a solution. The sample carrier includes the first carrier portion containing a dried sample and a second carrier portion affixed to the first carrier portion. The solution is collected in a vessel. A precipitate that includes a component of the first carrier portion is formed in the solution and removed from the solution.

In still another aspect, the invention features a sample carrier for storing a dried sample of a received fluid. The sample carrier includes a first carrier portion, a second carrier portion and a third carrier portion. The first carrier portion is configured to receive a fluid sample and includes a material that adsorbs the fluid sample and that is indissolvable in a solvent. The second carrier portion is affixed to the first carrier portion and includes a material that dissolves upon application of the solvent. The third carrier portion is affixed to the second carrier portion and is separated from the first carrier portion by the second carrier portion. The third carrier portion includes a material that is indissolvable in the solvent. The first carrier portion contains a dried sample and is separated from the third carrier portion upon application of the solvent to the second carrier portion.

In yet another aspect, the invention features a method of extracting a fluid sample from a dried sample. A second carrier portion of a sample carrier is dissolved into a solution. The sample carrier includes a first carrier portion containing a dried sample, a third carrier portion and the second carrier portion disposed between the first and third carrier portions. The first carrier portion and a solution are collected in a vessel. A precipitate is formed in the solution and includes a component of the second carrier portion. The precipitate is removed from the solution.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

FIG. 3A is a cross-sectional side view of a single collection region for the sample carrier of FIG. 2 when clamped to a sample collection plate.

FIG. 3B shows the cross-sectional side view of FIG. 3A after applying a solvent and dissolving the collection region into a solution that includes the extracted sample.

FIG. 5A and FIG. 5B show a top view and a cross-sectional side view, respectively, of a single collection region for another embodiment of a sample carrier for biological fluid sampling when clamped to a sample collection plate.

FIG. 5C and FIG. 5D shows the top view of FIG. 5A and cross-sectional side view of FIG. 5B, respectively, after applying a solvent and dissolving the collection region into a solution that includes the extracted sample.

FIG. 6 shows another embodiment of a sample carrier for storing a dried sample of a received fluid according to the invention.

FIG. 7A shows a cross-sectional side view of a single collection region of another embodiment of a sample carrier for biological fluid sampling when clamped to a sample collection plate.

FIG. 7B shows the cross-sectional side view of FIG. 7A after applying a solvent and dissolving a border region to thereby release the collection region into a vessel.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, various embodiments relate to a sample carrier for storing a dried sample of a received fluid sample. By way of examples, the fluid sample can be a biological fluid sample or a non-biological aqueous sample. Other embodiments are related to a method of extracting a fluid sample from a dried sample. The method includes dissolving a portion of a carrier that contains the dried sample into solution. The solution is captured in a vessel and another solution, for example, water, is added to the vessel so that unwanted sample constituents (e.g., blood proteins) and collection material precipitate out of the solution. The precipitate is removed by any one of a variety of techniques such as centrifugation or filtration, and the supernatant is made available for analysis, for example, by transfer to another vessel as in a typical work flow for protein precipitation (PPT). In alternative embodiments, a portion of the sample carrier is dissolved to release another portion of the sample carrier that contains the dried sample from the remainder of the sample carrier. For example, the dissolving portion can be a border (e.g., an annulus) that separates the portion containing the dried sample from the bulk of the sample carrier. The various embodiments of the method eliminate the need to punch out dried sample spots from the sample carrier and therefore avoid multiple problems associated with the punch process.

In the descriptions of various embodiments below, reference is made to sample carriers for DBS sampling. It will be recognized that the devices and methods of the invention can also be used with sample carriers for dried sample spots of other fluids such as other biological fluids. For example, other biological fluids include urine, saliva, plasma, serum and cerebrospinal fluid.

Figure 1:
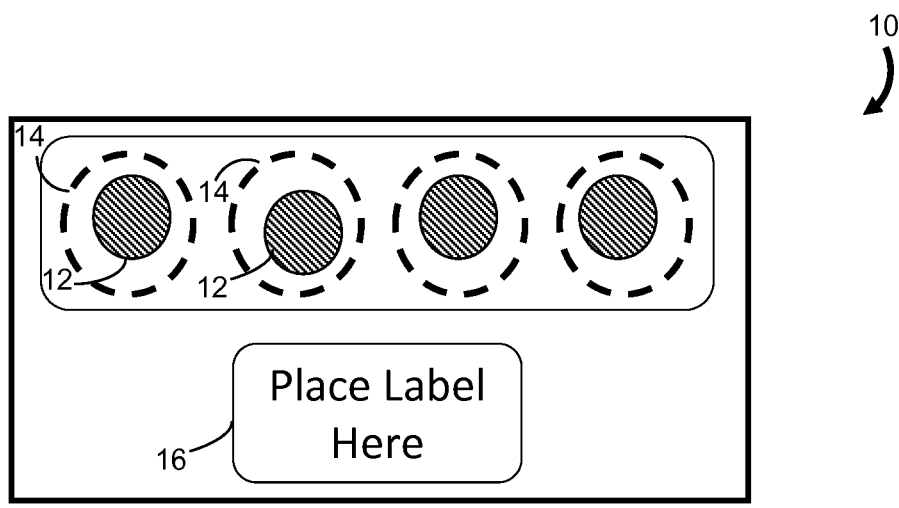
FIG. 1 is an illustration of a conventional dried blood spot card for acquiring blood samples.

FIG. 1 shows a conventional DBS card 10 for acquiring blood samples 12 to be dried and shipped to a laboratory or test site. The DBS card 10 is typically fabricated from filtration paper, polymer, glass fibers or other material known in the art for acquiring dried sample spots. The card 10 includes circular markings 14 that surround areas to receive blood samples 12. The markings 14 provide guidance for where to deposit the blood samples 12 on the sample carrier 10. The carrier material outside the circular markings 14 is the same as the carrier material encircled by the markings 14. Sample location and density can vary within each circular marking 14. An identification (ID) field 16 is located adjacent to each marking 14 to allow information regarding each sample 12 to be recorded, for example, by attaching a label.

For repeatability of analytical results, sampling of the entire dried blood spot 12 is required. Conventional techniques include punching the blood spots 12 from sample cards 10. Care must be taken to punch the entire blood spot 12 from the card 10 otherwise the repeatability and accuracy of the analytical measurements can vary. Moreover, if the punch tool makes contact with a blood spot 12, subsequent use of the punch tool can result in carryover and potentially adversely affect subsequent measurements. The process of punching the spots 12 requires special attention and can limit the speed at which measurements can be performed.

Figure 2:
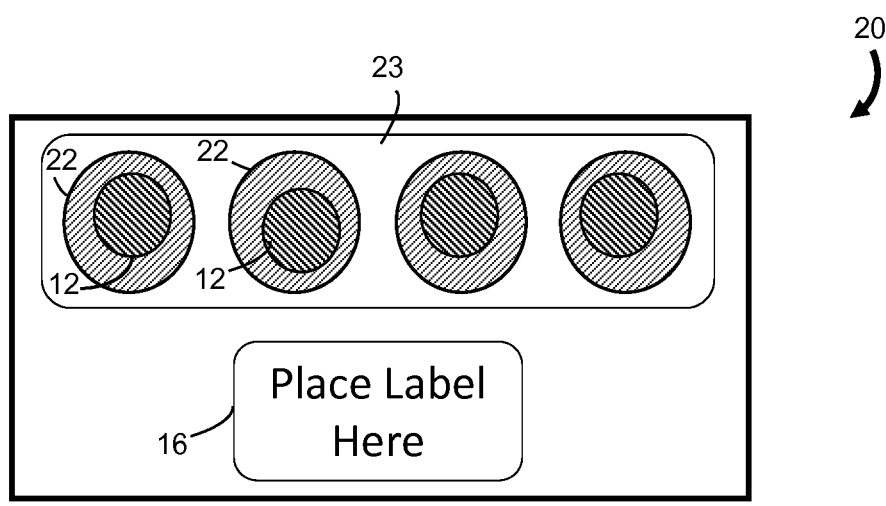
FIG. 2 shows an embodiment of a sample carrier for storing a dried sample of a received fluid according to the invention.

Referring to FIG. 2, an embodiment of a sample carrier 20 for storing a dried sample of a received fluid according to the invention is shown. The sample carrier 20 is in the form of a card and includes a plurality of first carrier portions (collection regions 22) disposed in a second carrier portion 23. Each collection region 22 has an area sufficient to receive a blood sample of known volume. For example, each collection region 22 may be a circular region having a circumference similar to the circumference of the circular markings 14 for the DBS card 10 of FIG. 1. The circumference of each collection region 22 may be indicated by a visible marking to enable a clinician to accurately apply a blood sample. Alternatively, each collection region 22 may have a color or texture to distinguish it from the surrounding portion 23 of the sample carrier 20.

The collection regions 22 comprise a material that dissolves in one or more solvents, such as acetonitrile, whereas the surrounding regions of the sample carrier 20 are indissolvable in the solvents. The collection regions 22 may be formed of various material structures such as membranes, sponges, fibers or a combination of two or more material structures. In a preferred embodiment, the collection regions 22 are membrane-like filters fabricated, for example, from cellulose acetate. Optionally, the cellulose acetate may be combined, or mixed, with one or more other materials according to the particular sampling application. In an alternative embodiment, the collection regions 22 are formed as polysulfone filters. These collection region materials are hydrophilic and are compatible with aqueous and alcoholic solutions. In addition, the collection region materials are particularly suitable for adsorption of blood samples and other aqueous biological samples due to their lack of adsorption of analytes, proteins and immunoglobulins. Moreover, solvents such as acetonitrile, acetone, dimethyl sulfoxide (DMSO), dimethylformamide (DMF) and dichloromethane (DCM) can be used either alone or in combination with water to easily solubilize most analytes and to facilitate the extraction of the analytes from residual fibers, precipitated proteins and cell debris.

After the applied blood samples dry, the sample carrier 20 is transported to the test site where it is secured to a sample collection plate. Laboratories and test sites typically employ work flows based on the transfer, addition or evaporation of liquid samples. In the following description, protein precipitation (PPT) is the technique employed in sample preparation. According to one PPT technique, one part plasma is added to three parts acetonitrile to yield a solution of 75% acetonitrile.

Figure 4:
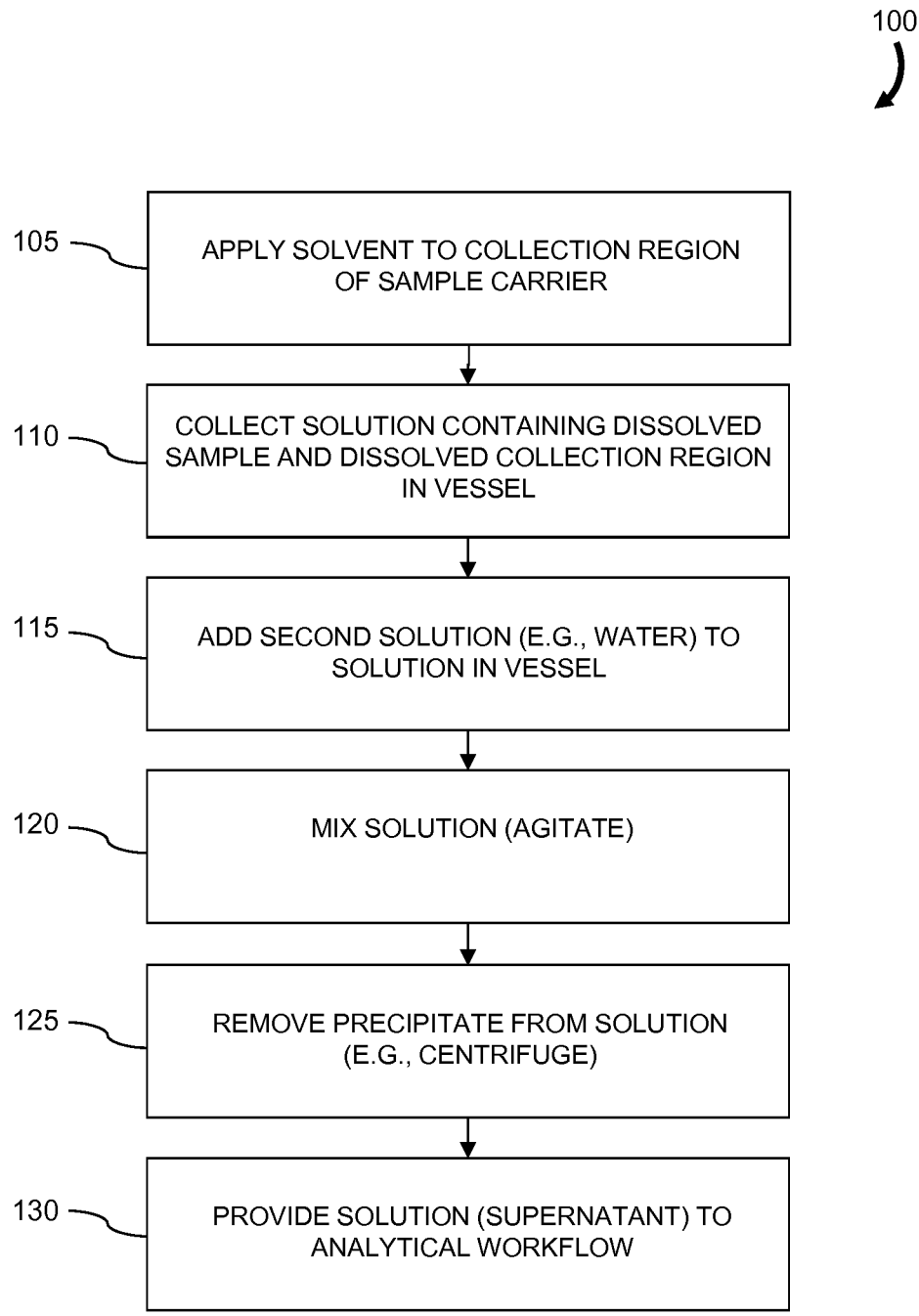
FIG. 4 is a flowchart representation of an embodiment of a method of extracting a blood sample from a dried blood spot on a sample carrier.

FIG. 3A illustrates a cross-sectional side view of a single collection region 22 in the sample carrier 20 when clamped to a sample collection plate 26. Reference is also made to FIG. 4 which shows a flowchart representation of an embodiment of a method 100 of extracting a blood sample from a dried blood spot on a sample carrier. A reservoir 28 containing acetonitrile 30 (or other solvent) is positioned against the upper surface of the surrounding portion 23 of the sample carrier 20 so that the solvent is applied (step 105) to the collection region 22. Preferably, the solvent is also applied to the nearby region of the surrounding portion 23 to ensure that the entire collection region 22 dissolves in the solvent. Features 32 in the figure indicate the contact interface between the upper surface of the surrounding portion 23 and the lower surface of the reservoir 28, and the contact interface between the lower surface of the surrounding portion 23 and the upper surface of the sample collection plate 26. Preferably, sufficient force is applied to maintain the components securely against each other so that the solvent is restricted to the desired regions of the sample carrier 20. In other embodiments, one or more gaskets may be provided at one or both of the contact interfaces 32 to ensure a fluidic seal.

The acetonitrile dissolves the collection region 22 and the resulting solution 34, including the extracted sample, is collected (step 110) in a vessel 36 (e.g., a sample well) as shown in FIG. 3B. Water is added (step 115) to the solution 34 in the vessel to reduce the percentage of acetonitrile. The sample collection plate and vessel structure is agitated (step 120) to mix the water and solution 34. By way of example, the acetonitrile composition may be reduced to a value within a range of 50% to less than 75% according to the polarity or solubility of the analytes to be measured. Optionally, an acid or base can be added with the water to the solution to mitigate drug protein interactions. At these acetonitrile concentrations, blood proteins and the cellulose acetate precipitate from the mixed solution. The precipitate is removed (step 125) from the solution 34 by various techniques. For example, centrifugation per standard PPT workflows can be applied to produce a pellet, making the supernatant easy to remove from the vessel 36. Alternatively, a filtration process can be used. The dissolution process may result in some particulate matter from the collection 22 region being present in the solution 34; however, the centrifugation or filtration processes can also assist in the removal of the particulate matter. In other examples, alternative separation techniques can be used to remove the dissolved collection region material that may otherwise have adverse effects on the analytical equipment (e.g., analytical column of a liquid chromatography system). Size exclusion chromatography (SEC) is an example of molecular weight size separation techniques that may be used. In SEC techniques, large molecules such as polymers cannot diffuse into small pores on the stationary phase (i.e. the large molecules are physically excluded from pores). Thus the large molecules are separated from small molecules which penetrate into the pores. The pore size of the stationary phase is selected to achieve efficient separation between the analytes of interest and the large interfering molecules, such as dissolved collection region material and the interference from a sample matrix (e.g. proteins in blood). A magnetic capture technique is also useful for achieving separation. According to the technique, magnetic materials such as microbeads or microrods are attached to the collection region material. Thus the collection region material is captured and separated through application of a magnetic field. After the precipitate is removed by a separation process, the supernatant is provided (step 130) to an analytical workflow, for example, by transfer to another plate and well.

One or more steps of the method 100 can be performed using a robotic system. Moreover, it should be appreciated that the method 100 can be performed for each collection region on the sample carrier 20 in a simultaneous manner. Preferably, a number of dried blood spots 12, each one provided in a respective one of collection regions 22 on the sample carrier 20, can be processed at the same time in an automated manner for increased analytical efficiency.

In the embodiments described above, each collection region 22 dissolves and leaves an opening in the surrounding region 23 of the sample carrier 20. In other embodiments, the collection region is supported by a separate structure. For example, the collection region 22' can be disposed on a screen or mesh 42 as shown for a single collection region 22' in the top and side views of FIG. 5A and FIG. 5B, respectively. After the solvent is applied and the collection region 22' dissolves, the screen 42 remains fixed to or extending into the surrounding portion 23 of the sample carrier as shown in the top and side views of FIG. 5C and FIG. 5D, respectively. Alternatively, the structure can be, by way of examples, fibers, a membrane or one or more other features that support or secure the collection region within the surrounding portion 23 of the sample carrier. In some embodiments, the structure also dissolves upon application of the solvent so that materials from both the collection region 22' and the structure are present in the solution collected in the vessel.

Referring to FIG. 6, another embodiment of a sample carrier 50 for storing a dried sample of a received fluid according to the invention is shown. The sample carrier 50 includes second carrier portions in the form of dissolvable border regions 52. Each border region 52 has an annular shape and separates a collection region 54 (i.e., a first carrier portion) from the surrounding portion 23 (i.e., a third carrier portion) of the sample carrier 50. A visible marking may be provided along the inner or outer circumference of each border region 52 to designate the collection regions 54. Alternatively, at least one of the border regions 52 or the collection regions 54 can have a color or texture to distinguish them from the remainder of the sample carrier 50.

In this embodiment, the border regions 52 include a material that dissolves in a solvent; however, the collection regions 54 and the remainder of the sample carrier 50 are indissolvable in the solvent. In preferred embodiments, the border regions 52 comprise cellulose acetate or polysulfone membranes.

Figure 8:
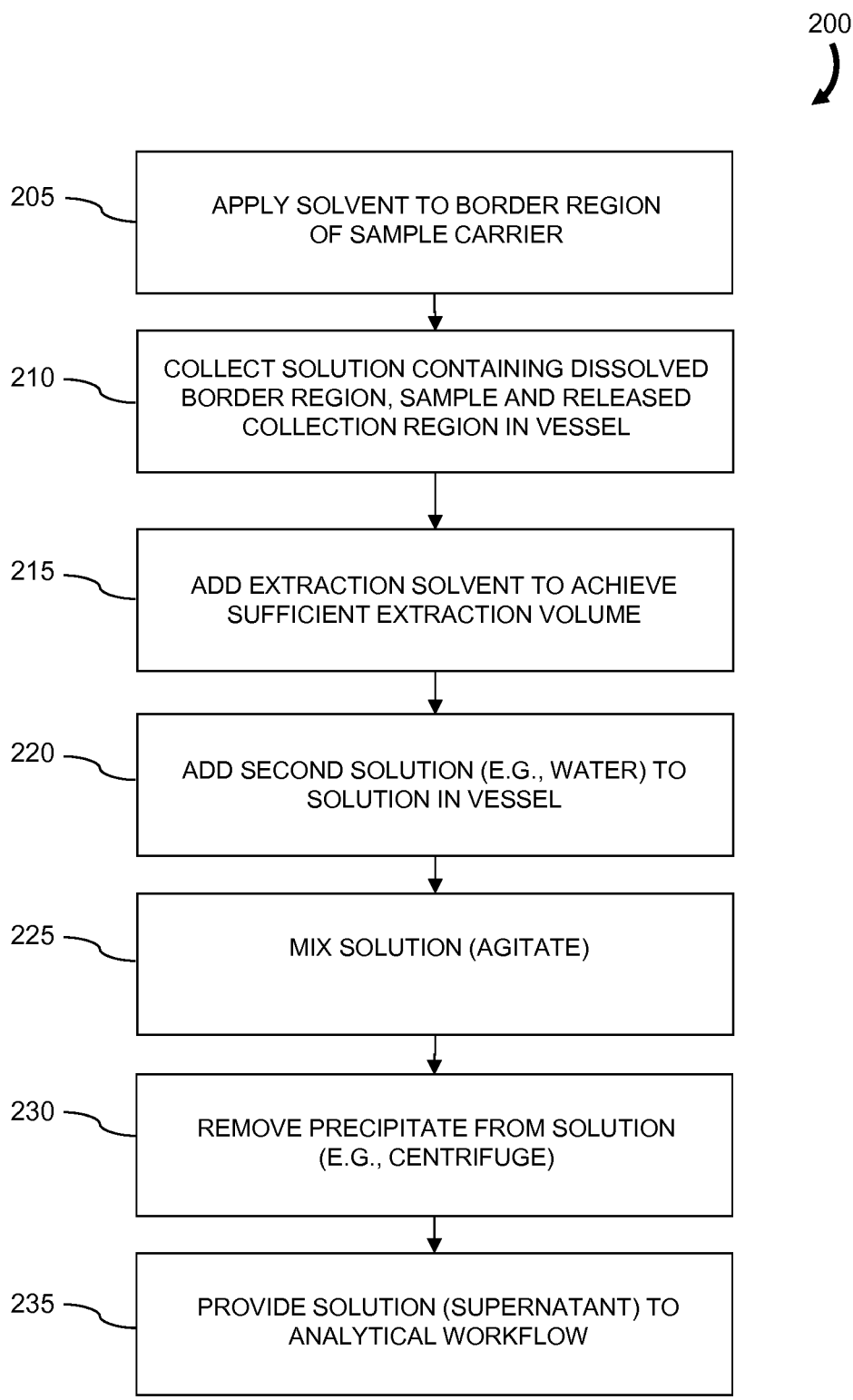
FIG. 8 is a flowchart representation of another embodiment of a method of extracting a blood sample from a dried blood spot on a sample carrier.
Figure 9A:
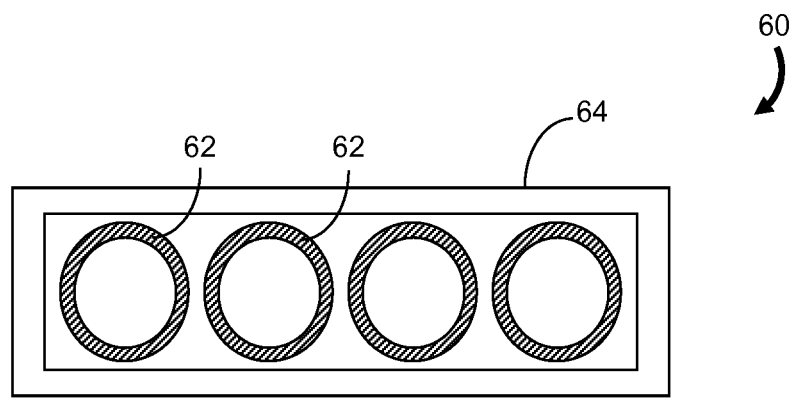
FIG. 9A and FIG. 9B are a bottom view and a side view, respectively, of a tool for applying solvent to the border regions of the sample carrier of FIG. 6.
Figure 9B:
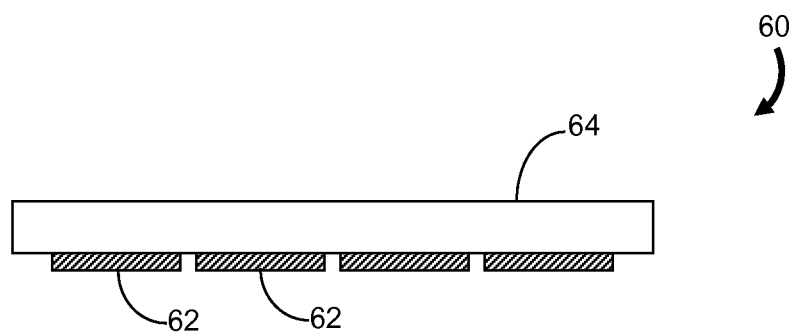

FIG. 7A illustrates a cross-sectional side view of a single collection region 54 and border region 52 in the sample carrier 50 when clamped to a sample collection plate 26 and FIG. 8 provides a flowchart representation of an embodiment of a method 200 of extracting a blood sample from a dried blood spot on a sample carrier. A reservoir 28 containing a solvent 30 is positioned against the upper surface of the surrounding portion 23 of the sample carrier 50 so that the solvent 30 is applied (step 205) to the border region 52. As shown, the solvent 30 is also applied to the collection region 54; however, in other embodiments, the opening at the base of the reservoir 28 is configured to approximately confine application of the solvent 30 to the border region 52. For example, the reservoir base may have an annular opening sized according to the dimensions of the border region 52. In another alternative, a tool 60 having a number of solvent applicators 62 secured in a frame 64 is used to apply the solvent. The tool 60 is shown in the bottom and side views of FIG. 9A and FIG. 9B, respectively. Each applicator 62 is a ring-shaped sponge or similar absorbent material that is secured within a corresponding annular channel in the frame 64. To apply solvent to the border regions 52, the sample carrier 50 is clamped to a sample collection plate that is configured to receive the tool 60. The tool 60 is first lowered into a long reservoir (not shown) that holds the solvent so that each sponge applicator 62 absorbs solvent. The tool 60 is then removed from the reservoir and positioned with respect to the sample collection plate so that the solvent applicators 62 are in contact with the border regions 52 to initiate the dissolving process which releases the sample collection region 54 into the vessel 36 as shown in FIG. 7B.

Referring to FIG. 7B and again to FIG. 8, after the solvent dissolves a border region 52, the collection region 54 containing the sample 12 is released from the sample carrier 50 and collected (step 210) in the vessel 36 along with the solution 56 containing the dissolved border region. There may be an insufficient solution volume to obtain a desired extraction volume, therefore extraction solvent can be added (step 215) to the solution 56 to obtain the desired volume. Water is added (step 220) to the vessel 36 to reduce the percentage of acetonitrile in the solution 56. The sample collection plate 26 and vessel 36 are agitated (step 225) to mix the water and solution, and to assist in the extraction of the sample 12 from the collection region 54. The precipitate that forms in the solution 56 is removed (step 230) by any of a variety of known techniques and the supernatant is then made available (step 235) to the analytical workflow.

Figure 10:
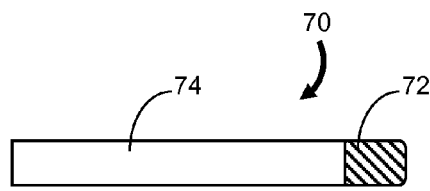
FIG. 10 shows another embodiment of a sample carrier for storing a dried sample of a received fluid according to the invention.
Figure 11:
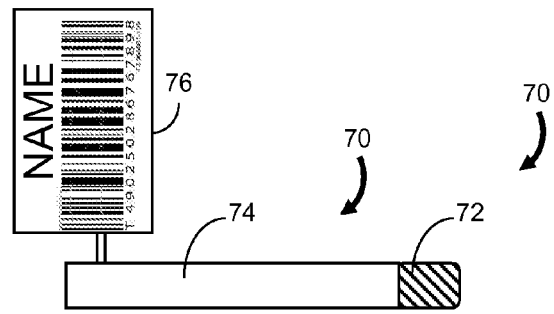
FIG. 11 shows the sample carrier of FIG. 10 with an attached identification label.

Referring to FIG. 10, another embodiment of a sample carrier 70 for storing a dried sample of a received fluid according to the invention is shown. The sample carrier 70 is in the form of a linear segment (e.g., dipstick) that includes a first carrier portion (i.e., collection region) 72 to receive a fluid sample. The first carrier portion is formed from a material that adsorbs the fluid sample and dissolves upon the application of a solvent. A second carrier portion 74 is attached to the first carrier portion 72 and is fabricated from a material that is indissolvable in the solvent. The second carrier portion 74 allows a clinician to hold the sample carrier 70 during various aspects of sample collection and processing without touching the collection region 72. In addition, the second carrier portion 74 provides a means for attaching an identifier during sample acquisition or processing. FIG. 11 shows an example of an identification label 76 attached to the sample carrier 70.

Figure 12A:
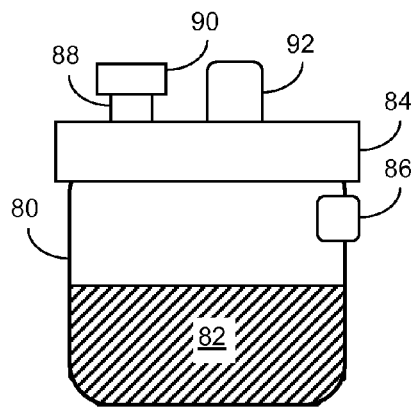
FIG. 12 A is an illustration of a container for holding a fluid to be sampled with the sample carrier of FIG. 10.
FIG. 12B shows the cap of the container of FIG. 12A inverted to receive the sample carrier of FIG. 10.
FIG. 12C is a view looking down onto the inverted cap shown in FIG. 12B.
Figure 12B:
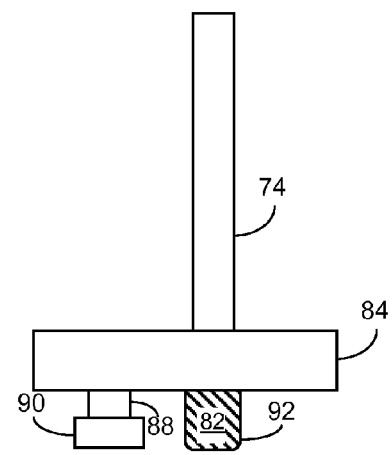
Figure 12C:
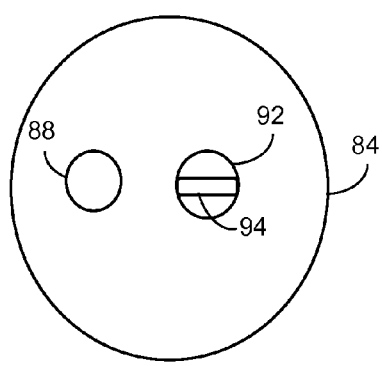

FIGS. 12A to 12C show how the sample carrier 70 of FIG. 10 may be used during aspects of a sample collection procedure. Referring to FIG. 12A, a container 80 holds a fluid 82 to be sampled and analyzed. By way of a specific example, the fluid 82 may be urine obtained at a doctor's office. A container cap 84 is screwed on to the top of the container 80 before sending the volume of fluid 82 to a laboratory for analysis. At the laboratory, a clinician shakes the container 80 to ensure that constituents in the fluid are properly mixed before subsequent processing. A tab 86 covering a small opening on the side of the container 80 is removed to allow air to enter the container while the fluid 82 is subsequently poured from a pour spout 88 (after removing a spout cap 90) on the top of the container cap 84. The poured fluid may be used for other testing or analysis, or may be treated as excess fluid and discarded. Care is taken to preserve a sufficient volume of fluid to fill a dip volume portion 92 extending from the cap 84.

FIG. 12B shows how the cap 84 may be inverted for placement on a flat surface with fluid contained in the dip volume portion. The dipstick sample carrier 70 is then inserted through a slot 94 in the container cap as shown in a top side view of the inverted cap in FIG. 12C so that the collection region 72 is fully immersed in the fluid 82 contained in the dip volume portion 92. The sample 70 carrier remains inserted for a sufficient time (e.g., 5 seconds) to ensure adequate adsorption of the fluid 82 into the collection region 72 before the sample carrier 70 is removed through the slot 94 and allowed to dry. The dimensions of the slot 94 are closely matched to the dimensions of the cross-section of the collection region 72 so that any excess fluid that forms a meniscus on the surface of the collection region 72 is removed as the sample carrier 70 is retracted. The removed sample carrier 70 can be placed in a holder or device that allows the collection region 72 to dry before further processing.

Although described above as occurring at the laboratory, the acquisition of the fluid sample onto the dipstick sample carrier 70 can be instead performed at the location where the fluid is first acquired, e.g., at the doctor's office. In this instance, the dipstick sample carrier 70 can be placed in a suitable transportation container after a sufficient drying time and sent to the laboratory or test facility for analysis.

The dipstick sample carrier 70 with the dried sample in the collection region can be processed to extract a fluid sample in a variety of ways consistent with those described above for other forms of sample carriers. For example, a solvent is applied to dissolve the collection region 72 and the resulting solution can be processed to remove precipitate before providing the solution to an analytical workflow.

Figure 13:
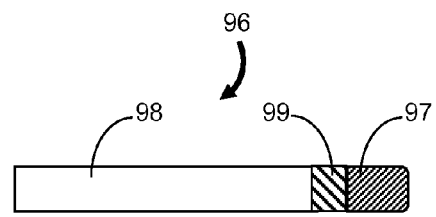
FIG. 13 shows another embodiment of a sample carrier for storing a dried sample of a received fluid according to the invention.

In an alternative embodiment of a dipstick sample carrier 96 shown in FIG. 13, the first carrier portion (i.e., collection region 97) and a third carrier portion 98 are indissolvable in a solvent while a second carrier portion 99 disposed along the linear segment between the other two portions 97 and 98 is dissolvable. In this embodiment, the dipstick sample carrier 96 is used in a similar manner to the dipstick carrier 70 of FIG. 10; however, application of the solvent during the extraction process results in the release of the collection region 97 into solution. Thus subsequent processing is similar to that described above with respect to FIGS. 7A and 7B for a sample carrier 50 having a dissolvable border region 52.

In further embodiments of the sample carriers described above, small particles are embedded in or provided on the surface of each collection region, border region or both collection and border regions. The particles can be nano scale particles to micron size particles and may include silica, zirconia, alumina, carbon, polymeric, porous, non-porous, salts or magnetic particles, or combinations of two or more types of particles. In some further embodiments, the particles are coated or derivatized. The particles can provide a useful function related to chromatographic analysis and may include a selective sorbent. Upon dissolving the collection regions, the particles are released into the solution in the vessels and may be further processed. One particular type of particle material useful for this purpose is an ion exchanger material. By way of a specific example, the collection regions can include particles to remove interfering substances from the sample. For PPT, the particles can be Ostro® available from Waters Corporation of Milford, Mass. used to remove phospholipids from the extracted sample. The phospholipids, trapped on the Ostro particles, can then be removed with the pellet resulting from centrifugation as described above as part of a standard PPT workflow.

Evaluation of DBS Samples

DBS samples were prepared on 5-mm diameter cellulose acetate collection discs by spotting 3 μL of rat whole blood that included eight test analytes. The blood spots were air-dried at least for 2 hours (typically for 16 hours) before further processing. Subsequently, each DBS sample was placed in a microcentrifuge tube and then 100 μL of dissolution solution was added to each tube. The dissolution solutions included water/acetonitrile (ACN) mixtures with and without 0.1% formic acid (FA). The cellulose acetate discs immediately dissolved in the dissolution solutions to form milky liquid mixtures. Table 1 lists the volume and composition of the eight dissolution solutions (#1 through #8) used in the evaluation.

Figure 15:
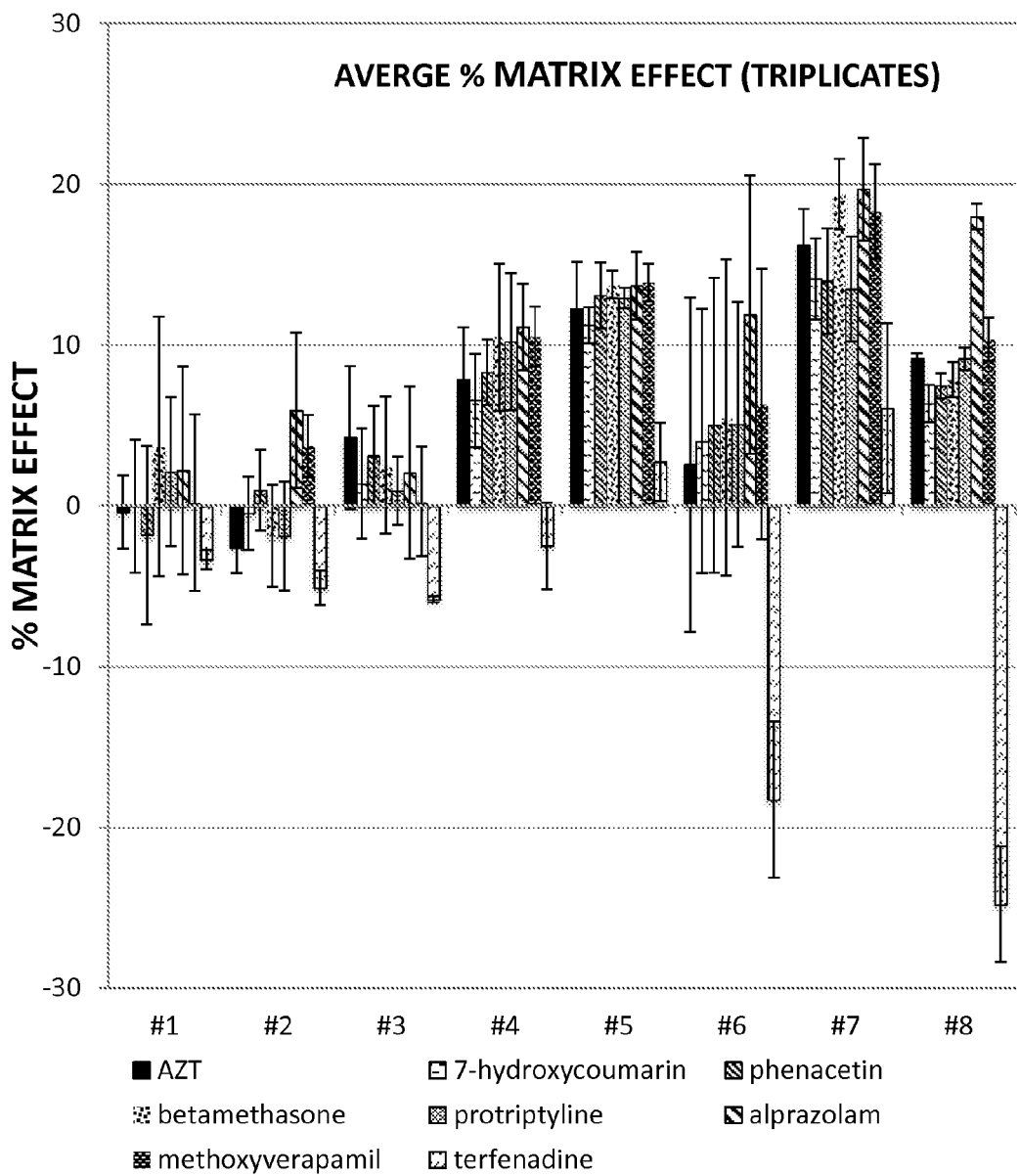
FIG. 15 is a graphical representation of the average percent matrix effect for the evaluation data corresponding to FIG. 14.

FIG. 15 show the average percent recovery and the average percent matrix effect, respectively, of eight analytes for three replicates. A matrix effect value was determined by comparing the response of an analyte spiked into extracted matrix blank with the response of the analyte spiked into matrix-free solution. This value illustrates how the sample matrix influences the analyte response.

$$\% \text{ Matrix Effect} = \left( \frac{Response_{analyte\ in\ extracted\ matrix\ blank}}{Response_{analyte\ in\ matrix-free\ solution}} - 1 \right) \times 100$$

While the invention has been shown and described with reference to specific embodiments, it should be understood by those skilled in the art that various changes in form and detail may be made therein without departing from the spirit and scope of the invention as recited in the accompanying claims. For example, a sample carrier according to various embodiments of the invention can be constructed so that the carrier area surrounding the collection regions is fabricated from a material that is impermeable to biological fluids. In this manner the volume available for receiving the applied biological fluid sample can be accurately defined. Consequently, by saturating an entire collection region with the biological fluid sample, a known sample volume is acquired.

What is claimed is:

1. A sample carrier for storing a dried sample of a received fluid, comprising:
   a first carrier portion to receive a fluid sample and comprising a material that adsorbs the fluid sample and dissolves upon application of a solvent; and
   a second carrier portion affixed to the first carrier portion and comprising a material that is indissolvable in the solvent, wherein the first carrier portion and a dried sample contained therein are dissolved into a solution upon application of the solvent to the first carrier portion.

2. The sample carrier of claim 1 wherein the fluid sample is a biological fluid sample.

TABLE 1

| | #1 | #2 | #3 | #4 | #5 | #6 | #7 | #8 |
|---|---|---|---|---|---|---|---|---|
| Dissolution solution volume | 100 μL | 100 μL | 100 μL | 100 μL | 100 μL | 100 μL | 100 μL | 100 μL |
| Dissolution solution composition (v/v) | 100% ACN | 100% ACN 0.1% FA | 80% ACN | 80% ACN 0.1% FA | 80% ACN | 80% ACN 0.1% FA | 80% ACN | 80% ACN 0.1% FA |
| Volume of water (or water + FA) | 400 μL | 400 μL 0.1% FA | 300 μL | 300 μL 0.1% FA | 100 μL | 100 μL 0.1% FA | 60 μL | 60 μL 0.1% FA |
| Reprecipitation composition (v/v) | 20% ACN | 20% ACN 0.1% FA | 20% ACN | 20% ACN 0.1% FA | 40% ACN | 40% CAN 0.1% FA | 50% ACN | 50% ACN 0.1% FA |

Figure 14:
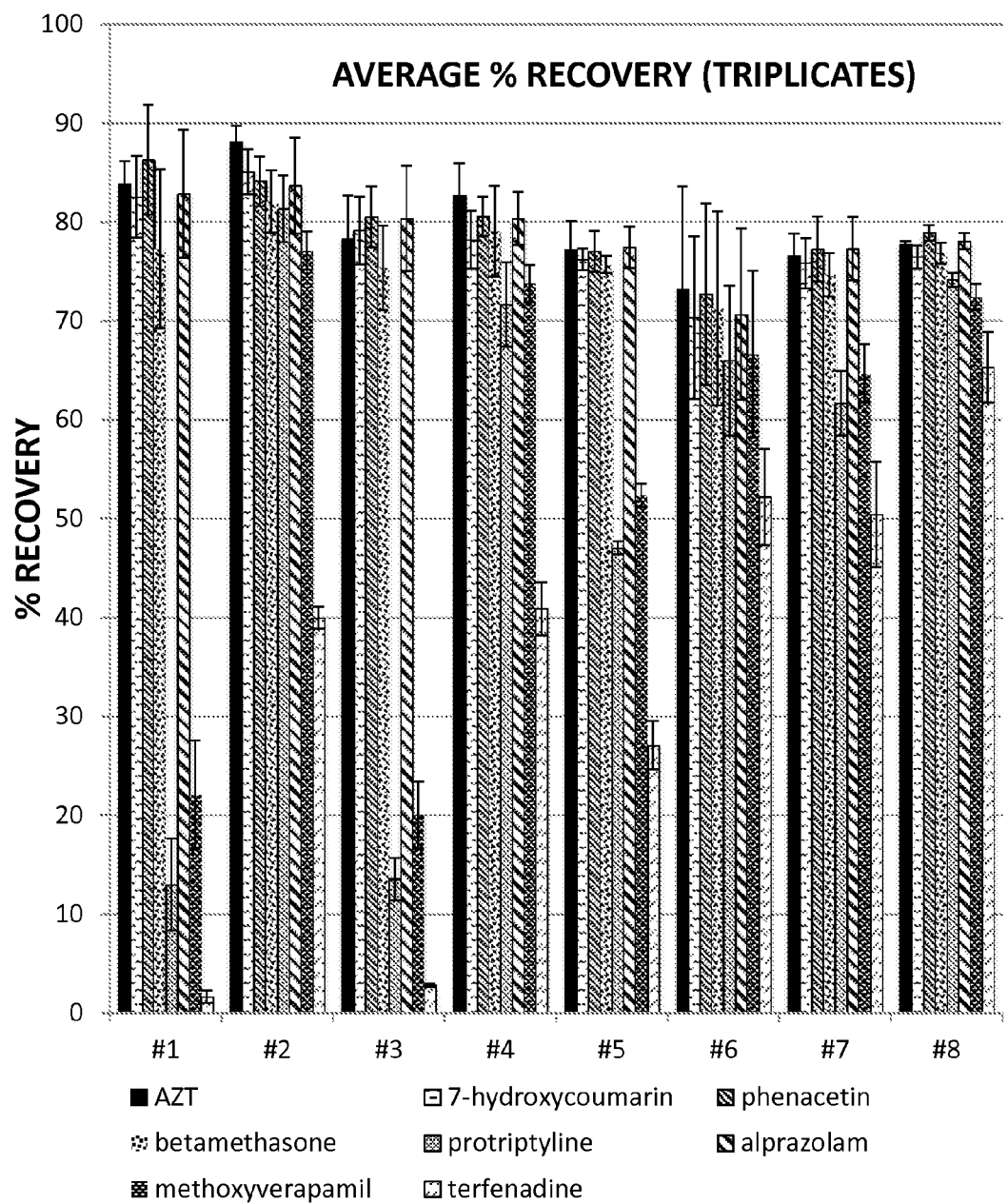
FIG. 14 is a graphical representation of evaluation results for the average percent recovery for each of eight test analytes according to eight different dissolution solutions.

Water was added to each mixture to reprecipitate the cellulose acetate. Table 1 lists the volume of added water (or added water and 0.1% FA if the dissolution solution contained FA) and the resulting solution compositions. After the each microcentrifuge tube was centrifuged (typically at 15000 rpm for 10 minutes) to separate the solid cellulose acetate from the liquid, an aliquot of clear solution was removed for further analysis. The aliquot can be directly injected for LC-MS analysis or diluted first to change the solution composition and then analyzed. In this evaluation, all the aliquots were diluted in acetonitrile to achieve 70% acetonitrile solutions prior to LC-MS injection. FIG. 14 and 3. The sample carrier of claim 1 wherein the first carrier portion is configured to hold a predetermined volume of the fluid sample.

4. The sample carrier of claim 1 wherein the first and second carrier portions are disposed in a sample card in which the second carrier portion surrounds the first carrier portion.

5. The sample carrier of claim 1 wherein the first and second carrier portions are configured along a linear segment and wherein the first carrier portion is disposed at one end of the linear segment and the second carrier portion is disposed at an opposite end of the linear segment.

6. The sample carrier of claim 1 wherein the second carrier portion is impermeable to the fluid sample.

7. The sample carrier of claim 1 wherein the solvent is selected from a group of solvents consisting of acetonitrile, acetone, dimethyl sulfoxide, dimethylformamide and dichloromethane.

8. The sample carrier of claim 1 wherein the first carrier portion is indissolvable in an aqueous solution.

9. The sample carrier of claim 1 wherein the first carrier portion is formed of a material comprising cellulose acetate.

10. The sample carrier of claim 1 wherein the first carrier portion is formed of a material comprising polysulfone.

11. A method of extracting a fluid sample from a dried sample, the method comprising:
dissolving a first carrier portion of a sample carrier into a solution, the sample carrier comprising the first carrier portion and a second carrier portion affixed to the first carrier portion, the first carrier portion containing a dried sample;
collecting the solution in a vessel;
forming a precipitate in the solution, the precipitate comprising a component of the first carrier portion; and
removing the precipitate from the solution.

12. The method of claim 11 wherein the fluid sample is a biological fluid sample.

13. The method of claim 11 wherein dissolving the first carrier portion comprises applying a solvent to the first carrier portion.

14. The method of claim 13 wherein applying a solvent comprises applying a solvent from a group of solvents consisting of acetonitrile, acetone, dimethyl sulfoxide, dimethylformamide and dichloromethane.

15. The method of claim 11 wherein forming the precipitate in the solution comprises providing an additional solution to the solution in the vessel.

16. The method of claim 15 wherein the additional solution is water.

17. The method of claim 12 wherein the dried sample is a dried blood sample.

18. The method of claim 17 wherein the precipitate further comprises a blood protein.

19. The method of claim 11 wherein removing the precipitate comprises centrifuging the solution.

20. The method of claim 11 wherein removing the precipitate comprises filtering the solution.

21. A sample carrier for storing a dried sample of a received fluid, comprising:
a first carrier portion to receive a fluid sample and comprising a material that adsorbs the fluid sample and that is indissolvable in a solvent;
a second carrier portion affixed to the first carrier portion and comprising a material that dissolves upon application of the solvent; and
a third carrier portion affixed to the second carrier portion and being separated from the first carrier portion by the second carrier portion, the third carrier portion comprising a material that is indissolvable in the solvent, wherein the first carrier portion and a dried sample contained therein are separated from the third carrier portion upon application of the solvent to the second carrier portion.

22. The sample carrier of claim 21 wherein the fluid sample is a biological fluid sample.

23. The sample carrier of claim 21 wherein the first carrier portion is configured to hold a predetermined volume of the fluid sample.

24. The sample carrier of claim 21 wherein the first, second and third carrier portions are disposed in a sample card in which the second carrier portion surrounds the first carrier portion and separates the first carrier portion from the third carrier portion.

25. The sample carrier of claim 21 wherein the first, second and third carrier portions are configured as a linear segment and wherein the first carrier portion is disposed at one end of the linear segment, the third carrier portion is disposed at an opposite end of the linear segment and the second carrier portion is disposed between the first and third carrier portions.

26. The sample carrier of claim 21 wherein the solvent is selected from a group of solvents consisting of acetonitrile, acetone, dimethyl sulfoxide, dimethylformamide and dichloromethane.

27. The sample carrier of claim 21 wherein the first and third carrier portions are indissolvable in an aqueous solution.

28. The sample carrier of claim 24 wherein the second carrier portion is shaped as an annulus.

29. The sample carrier of claim 21 wherein the second carrier portion is formed of a material comprising cellulose acetate.

30. The sample carrier of claim 21 wherein the second carrier portion is formed of a material comprising polysulfone.

31. A method of extracting a fluid sample from a dried sample, the method comprising:
dissolving a second carrier portion of a sample carrier into a solution, the sample carrier comprising a first carrier portion, a third carrier portion and the second carrier portion disposed between the first and third carrier portions, the first carrier portion containing a dried sample;
collecting the first carrier portion and the solution in a vessel;
forming a precipitate in the solution, the precipitate comprising a component of the second carrier portion; and
removing the precipitate from the solution.

32. The method of claim 31 wherein the fluid sample is a biological fluid sample.

33. The method of claim 31 wherein dissolving the second carrier portion comprises applying a solvent to the second carrier portion.

34. The method of claim 33 wherein applying a solvent comprises applying a solvent from a group of solvents consisting of acetonitrile, acetone, dimethyl sulfoxide, dimethylformamide and dichloromethane.

35. The method of claim 31 wherein forming the precipitate in the solution comprises providing an additional solution to the solution in the vessel.

36. The method of claim 35 wherein the additional solution is water.

* * * * *

UNITED STATES PATENT AND TRADEMARK OFFICE
CERTIFICATE OF CORRECTION

PATENT NO. : 9,488,551 B2  
APPLICATION NO. : 14/375337  
DATED : November 8, 2016  
INVENTOR(S) : Pamela C. Iraneta et al.

It is certified that error appears in the above-identified patent and that said Letters Patent is hereby corrected as shown below:

In the Specification

Column 9, Table 1:
- In Column #6 of "Reprecipitation composition" line replace "40% CAN" with "40% ACN"

Signed and Sealed this
Seventh Day of March, 2017

Michelle K. Lee
*Director of the United States Patent and Trademark Office*